United States Patent [19]

Barner et al.

[11] Patent Number: 4,731,373
[45] Date of Patent: Mar. 15, 1988

[54] GLYCERIN DERIVATIVES AND INHIBITION OF BLOOD PAF

[75] Inventors: Richard Barner, Witterswil; Kasper Burri, Rheinfelden, both of Switzerland; Jean-Marie Cassal, Mulhouse, France; Paul Hadvary, Biel-Benken, Switzerland; Georges Hirth, Huningue, France; Klaus Müller, Münchenstein, Switzerland

[73] Assignee: Hoffman-La Roche Inc., Nutley, N.J.

[21] Appl. No.: 679,734

[22] Filed: Dec. 10, 1984

[30] Foreign Application Priority Data

Dec. 30, 1983 [CH] Switzerland .................. 6985/83
Sep. 20, 1984 [CH] Switzerland .................. 4498/84

[51] Int. Cl.⁴ .................. C07D 213/04; C07D 277/30; A61K 31/44; A61K 31/425
[52] U.S. Cl. .................. 514/365; 546/146; 546/147; 546/174; 546/175; 546/332; 546/335; 546/336; 546/337; 546/339; 546/342; 544/224; 548/204; 548/214; 548/236; 548/247; 548/341; 514/247; 514/307; 514/311; 514/357; 514/358; 514/372; 514/374; 514/378; 514/399
[58] Field of Search .................. 546/332, 337, 335, 342, 546/336, 339, 174, 175, 146, 147; 544/224; 548/236, 247, 341, 204, 214; 514/374, 357, 378, 307, 358, 399, 311, 247, 365, 372

[56] References Cited

U.S. PATENT DOCUMENTS 3,686,238 8/1972 Zaffaroal .................. 260/399
4,137,317 1/1979 Paris et al. .................. 546/90

FOREIGN PATENT DOCUMENTS 40039   11/1981 European Pat. Off. .
0070433  1/1983 European Pat. Off. .
0094186 11/1983 European Pat. Off. .
0094586 11/1983 European Pat. Off. .
0109255  5/1984 European Pat. Off. .
0146258  6/1985 European Pat. Off. .
1157910  7/1969 United Kingdom .

OTHER PUBLICATIONS

Chemical Abstracts 84: 10536f (1976).
Derwent 32,738.
Derwent 83-797365.
Derwent 21692S
Derwent 33708K
Derwent 84-079212

*Primary Examiner*—Henry R. Jiles
*Assistant Examiner*—Dale A. Bjorkman
*Attorney, Agent, or Firm*—Jon S. Saxe; Bernard S. Leon; William G. Isgro

[57] ABSTRACT

Glycerine derivatives of the formula

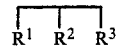

I wherein the residues $R^1$, $R^2$ and $R^3$ have the significance given in the description, and their hydrates, which inhibit blood platelet activating factor (PAF), are descried.

23 Claims, No Drawings

GLYCERIN DERIVATIVES AND INHIBITION OF BLOOD PAF

BRIEF SUMMARY OF THE INVENTION

The glycerine derivatives of the invention are compounds of the formula

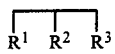

I wherein one of the residues $R^1$, $R^2$ and $R^3$ is group U of the formula —$OY^1$ or —$X^1$—C(O)—$(A^1)_n$—$Z^1$, another of the residues is group V of the formula —$OY^2$ or —$X^2$—C(O)—$(A^2)_p$—$Z^2$, and the remaining residue is group W of the formula —$X^3$T—($C_{2-6}$-alkylene)—$N^+$(Het)$Q^-$, wherein one of $X^1$, —$X^2$ and $X^3$ is oxygen or NH and the other two are oxygen,
$Y^1$ is $C_{10-26}$-alkyl or $C_{10-26}$-alkenyl,
$Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl,
$A^1$ and $A^2$, independently, are oxygen or NH,
n and p are the integer 1 or 0,
$Z^1$ is $C_{9-25}$-alkyl or $C_{9-25}$-alkenyl,
$Z^2$ is $C_{1-5}$-alkyl, $C_{2-5}$-alkenyl, phenyl or, when $(A^2)_p$ is not oxygen, $Z^2$ is also hydrogen,
T is carbonyl, C(O)O or C(O)NH or, when $X^3$ is oxygen, T is also methylene,
—$N^+$(Het) is a 5- to 7-membered aromatic heterocyclic residue, optionally with an additional O-, S- or N-atom, optionally with a fused benzene ring and optionally monosubstituted by hydroxy, $C_{1-4}$-alkyl, $C_{1-4}$-alkoxy, 2-(hydroxy or amino)-ethyl, carbamoyl or ureido, and
$Q^-$ is the anion of a strong inorganic or organic acid, and their hydrates.

DETAILED DESCRIPTION OF THE INVENTION

The glycerine derivatives of the invention are compounds of the formula

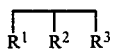

I wherein one of the residues $R^1$, $R^2$ and $R^3$ is group U of the formula —$OY^1$ or —$X^1$—C(O)—$(A^1)_n$—$Z^1$, another of the residues is group V of the formula —$OY^2$ or —$X^2$—C(O)—$(A^2)_p$—$Z^2$, and the remaining residue is group W of the formula —$X^3$T—($C_{2-6}$-alkylene)—$N^+$(Het)$Q^-$, wherein one of $X^1$, —$X^2$ and $X^3$ is oxygen or NH and the other two are oxygen,
$Y^1$ is $C_{10-26}$-alkyl or $C_{10-26}$-alkenyl,
$Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl,
$A^1$ and $A^2$, independently, are oxygen or NH,
n and p are the integer 1 or 0,
$Z^1$ is $C_{9-25}$-alkyl or $C_{9-25}$-alkenyl,
$Z^2$ is $C_{1-5}$-alkyl, $C_{2-5}$-alkenyl, phenyl or, when $(A^2)_p$ is not oxygen, $Z^2$ is also hydrogen,
T is carbonyl, C(O)O or C(O)NH or, when $X^3$ is oxygen, T is also methylene,
—$N^+$(Het) is a 5- to 7-membered aromatic heterocyclic residue, optionally with an additional O-, S- or N-atom, optionally with a fused benzene ring and optionally monosubstituted by hydroxy, $C_{1-4}$-alkyl, $C_{1-4}$-alkoxy, 2-(hydroxy or amino)-ethyl, carbamoyl or ureido, and
$Q^-$ is the anion of a strong inorganic or organic acid, and their hydrates.

The terms "alkyl" and "alkenyl" as used herein relate to straight-chain or branched, saturated or mono-unsaturated residues such as methyl, ethyl, propyl, isopropyl, 2-propenyl, butyl, isobutyl, hexadecyl, heptadecyl, octadecyl and octadecenyl, especially methyl and octadecyl. Examples of $C_{3-6}$-cycloalkyl residues $Y^2$ are cyclopropyl and cyclohexyl, examples of $C_{5-6}$-cycloalkenyl residues $Y^2$ are 2-cyclopentenyl and especially 2-cyclohexenyl. $C_{2-6}$-alkylene groups can be straight-chain or branched. Examples thereof are n-butylene, 2-methylpropylene and especially ethylene and propylene. Examples of heterocyclic residues —$N^+$(Het) are oxazolium, isoxazolium, pyridazinium, quinolinium, isoquinolinium and N-methylimidazolium and, especially, pyridinium and thiazolium.

Examples of anions of strong organic or inorganic acids are $C_{1-4}$-alkylsulfonyloxy, phenylsulfonyloxy, tosyloxy, camphor-10-sulfonyloxy or $Cl^-$, $Br^-$, $I^-$, $ClO_4^{--}$, $SO_4^{--}$, $PO_4^{---}$ and $NO_3Hu\ -$.

The compounds of formula I can be hydrated. The hydration can take place in the course of the manufacturing process or can occur gradually as a result of hygroscopic properties of an initially anhydrous compound of formula I.

The compounds of formula I contain at least one asymmetric C-atom and can, accordingly, exist as optically active enantiomers, as diastereomers or as mixtures thereof, for example, as racemates.

Preferred compounds of formula I are those in which $R^3$ is W.

More preferred compounds of formula I are those in which $R^1$ is octadecylcarbamoyloxy, $R^2$ is methoxyformamido, methoxy or especially methoxycarbonyloxy and/or in which $R^3$ is 4-(1-pyridinium chloride)-n-butyryloxy, 4-(1-pyridinium iodide)-n-butyryloxy, 4-(3-thiazolium chloride)-n-butyryloxy or especially 4-(3-thiazolium iodide)-n-butyryloxy.

Examplary of the preferred compounds of the invention are especially
3-[3-[[(R)-2-(methoxycarbonyloxy)-3-[(octadecylcarbamoyl)oxy]propoxy]carbonyl]propyl]thiazolium iodide, as well as,
3-[3-[[(S)-2-[(methoxycarbonyl)oxy]-3-[(octadecylcarbamoyl)oxy]propoxy]carbonyl]propyl]thiazolium iodide;
1-[3-[[(RS)-2-[(methoxycarbonyl)oxy]-3-[(octadecylcarbamoyl)oxy]propoxy]carbonyl]propyl]pyridinium chloride;
1-[3-[[(RS)-2-(1-methoxyformamido)-3-(octadecylcarbamoyloxy)propoxy]carbonyl]propyl]thiazolium chloride;
1-[3-[[(S)-2-[(methoxycarbonyl)oxy]-3-[(octadecylcarbamoyl)oxy]propoxy]carbonyl]propyl]pyridinium iodide;
1-[3-[[(R)-2-[(methoxycarbonyl)oxy]-3-[(octadecylcarbamoyl)oxy]propoxy]carbonyl]propyl]pyridinium chloride; and
3-[3-[[(RS)-2-methoxy-3-[(octadecylcarbamoyl)oxy]-propoxy]carbonyl]propyl]thiazolium chloride.

The compounds of formula I and their hydrates can be prepared by
(a) reacting a compound of the formula

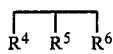    II wherein the residues $R^4$, $R^5$ and $R^6$ have the same significance as the residues $R^1$, $R^2$ and $R^3$, respectively, but in which a leaving group is present in place of the group $-N^+(Het)Q^-$,
with an amine of the formula N(Het), or
(b) reacting a compound of the formula

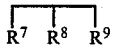    III wherein the residues $R^7$, $R^8$ and $R^9$ have the same significance as the residues $R^1$, $R^2$ and $R^3$, respectively, but in which a hydroxy or an amino group is present in place of one of the groups U and V,
with an acid of the formula $$Z^1-(A^1)_n-COOH \text{ or } Z^2-(A^2)_p-COOH \qquad IV$$

or a reactive derivatives thereof, or with an isocyanate of the formula $$Z^1NCO \text{ or } Z^2NCO \qquad V$$

or an imidazolide of the formula

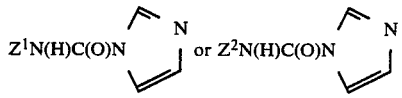    VI wherein $Y^1$, $Y^2$, $Z^1$, $Z^2$, $A^1$, $A^2$, T, N(Het), $Q^-$ n and p have the significance given above.

Examples of leaving groups present in the compounds of formula II are chlorine, bromine, iodine, mesyloxy, phenylsulfonyloxy and tosyloxy. The reaction of a compound II with an amine [N(Het)] can be carried out at a temperature up to the reflux temperature of the reaction mixture, conveniently at about 80° C., optionally in a solvent such as acetonitrile, nitromethane, or an aromatic hydrocarbon, for example, toluene or benzene.

Examples of reactive derivatives of the acids of formula IV are acid bromides or acid chlorides and anhydrides. The reaction of such an acid or of one of its reactive derivatives with a compound of formula III can be carried out in a known manner. An acid chloride or acid bromide can be reacted with a compound of formula III in a solvent in the presence of a base at a temperature of about 0° to 80° C. An anhydride can be reacted with a compound of formula III in the presence of a catalyst such as dimethylaminopyridine, conveniently in a solvent. Halogenated hydrocarbons such as chloroform or dichloroethane, can be used as solvents and organic bases such as triethylamine, quinoline or pyridine, or inorganic bases such as alkali or alkaline earth metal hydroxides, carbonates, or bicarbonates, for example, sodium carbonate, potassium bicarbonate or calcium carbonate, can be used as bases.

The reaction of a compound of formula III with an isocyanate of formula V or with a corresponding imidazolide of formula VI can be carried out in a solvent such as chloroform, acetone or dimethylformamide at a temperature between about 0° and 100° C., preferably at about 40°-60° C., conveniently in the presence of a catalyst such as a Lewis base, for example, triethylamine or diisopropylethylamine. If desired, the reaction can also be carried out without the addition of a solvent.

The compounds of formula II can be prepared from the compounds of formula VIII or IX and the compounds of formula III can be prepared from the compounds of formula VII according to the following Reaction Scheme:

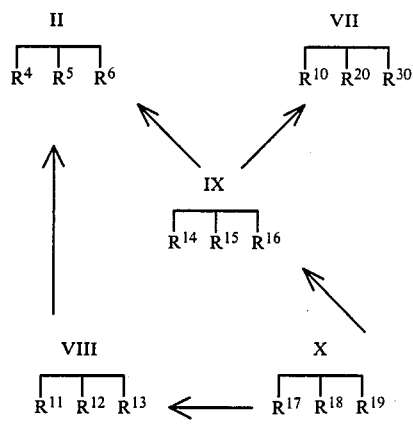

In the compounds of formula VII the residues $R^{10}$, $R^{20}$ and $R^{30}$ have the same significance as the residues $R^1$, $R^2$ and $R^3$, except that an optionally protected hydroxy or amino group or an azido group is present in place of one of the hydroxy groups U or V.

In the compounds of formula VIII the residues $R^{11}$, $R^{12}$ and $R^{13}$ have the same significance as the residues $R^1$, $R^2$ and $R^3$, except that an optionally protected hydroxy or amino group or an azido group is present in place of the group W.

In the compounds of formula IX one of the residues $R^{14}$, $R^{15}$ and $R^{16}$ is an optionally protected hydroxy or amino group or an azido group, another residue is a group U or V, and the remaining residue is the group W in which a leaving group is present in place of $-N^+(Het)Q^-$.

In the compounds of formula X one of the residues $R^{17}$, $R^{18}$ and $R^{19}$ is an optionally protected hydroxy or amino grop or an azido group, another residue is an optionally protected hydroxy group, and the remaining residue is the group U or V.

Examples of protected hydroxy and amino groups are ether groups such as benzyloxy, trityloxy or 2-tetrahydropyranyloxy, or succinimide, phthalimide, benzyloxycarbonylamino or t-butoxycarbonylamino.

For the preparation of a compound of formula II a compound of formula VIII in which, for example, $R^{13}$ is hydroxy can be reacted with a halide of the formula Hal—T—($C_{2-6}$-alkylene)—R, wherein R is a leaving group, Hal is a halogen atom and T has the above significance, in the presence of a base such as pyridine or with an isocyanate of the formula O=C=N—($C_{2-6}$-alkylene)—R.

Alternatively, a compound of formula IX in which, for example, $R^{14}$ is hydroxy can be converted into the corresponding compound of formula II in which $R^4$ is the group U or V, which can be carried out in the same manner as the conversion of a compound III into a compound I described above. Analogously, a compound of formula X in which, for example, $R^{17}$ is hydroxy and $R^{19}$ is a protected hydroxy or amino group can be converted into the corresponding compound of formula VIII in which $R^{11}$ is the group U or V.

An azido group or a protected hydroxy or amino group, for example, $R^{13}$, present in a compound of formula VIII can be converted into the free hydroxy or amino group in a known manner. A benzyl group can be cleaved by hydrogenolysis, for example, over palladium, a trityl group can be cleaved by means of trifluoroacetic acid or dilute hydrochloric acid, and a 2-tetrahydropyranyl group can be cleaved by means of dilute acid. An azido group can be converted into the amino group with a complex hydride such as lithium aluminum hydride or by means of hydrogen and palladium on carbon. Analogously, an azido group or a protected hydroxy or amino group present in a compound of formula VII, IX or X can be converted into the free hydroxy or amino group. In this manner a compound of formula VII in which, for example, $R^{10}$ is a protected hydroxy or amino group is converted into the corresponding compound of formula III in which $R^7$ is hydroxy.

To prepare a compound of formula IX in which, for example, $R^{16}$ is the group W in which a leaving group is present in place of $-N^+(Het)Q^-$, the corresponding compound of formula X in which $R^{19}$ is hydroxy can be treated in the same manner as described above for the conversion of a compound VIII into a compound of formula II.

The conversion of a compound of formula IX into a compound of formula VII can be carried out in the same manner as the conversion of a compound II into a compound I.

The compounds of formulas II, III and VII also form part of the invention.

The compounds of formula I and their hydrates inhibit blood platelet activating factor (PAF) and can be used in the control or prevention of illnesses, for example, vascular diseases, such as, thrombosis, heart infarct and angina pectoris, as well as bronchial asthma caused by allergy, and apoplexy. They are also useful as antiinflammatory and antirheumatic agents.

The inhibition of PAF can be demonstrated as follows:

Platelet-rich plasma (PRP) was and can be prepared by centrifugation of rabbit blood containing 1/10 volumes of 90 mM trisodium citrate. The aggregation of the blood platelets was measured with the aid of an aggregometer at 37° C. while stirring. Two (2) minutes after the addition of the test substance to the PRP, the platelet aggregation was triggered by a sub-maximum dosage of PAF (4 nM). The $IC_{50}$ value (in $\mu M$) given in the following Table corresponds to that concentration of the test substance which reduces to a half the aggregation of the blood platelets brought about by PAF.

| Product of Example: | 1 | 3 | 7a | 7b | 10 | 11 | 12 | 15 | 16 |
|---|---|---|---|---|---|---|---|---|---|
| $IC_{50}$ ($\mu M$) | 1.6 | 3 | 2 | 1.6 | 3 | 0.6 | 2 | 3 | 1.5 |
| Product of Example: | 20b | 21a | 21b | 21d | 21e | 21f | 24 | 26 | |
| $IC_{50}$ ($\mu M$) | 0.25 | 0.15 | 0.2 | 0.2 | 0.04 | 0.06 | 0.15 | 0.4 | |

As mentioned earlier, medicaments containing a compound of formula I or a hydrate thereof also form part of the present invention, as is a process for the preparation of such medicaments, which process comprises bringing one or more compounds of formula I or a hydrate thereof and, if desired, one or more other therapeutically valuable substances into a galenical form for administration.

The medicaments can be administered enterally, for example, orally in the form of tablets, coated tablets, dragees, hard and soft gelatine capsules, solutions, emulsions or suspensions, or rectally, for example, in the form of suppositories, or as a spray. The administration can, however, also be carried out parenterally, for example, in the form of solutions for injection.

For the manufacture of tablets, coated tablets, dragees and hard gelatine capsules, the active substance can be mixed with pharmaceutically inert, inorganic or organic excipients. As such excipients for tablets, dragees and hard gelatine capsules, there can be used, for example, lactose, maize starch or derivatives thereof, talc, stearic acid or its salts. For soft gelatine capsules, excipients, such as, for example, vegetable oils, waxes, fats, semi-solid and liquid polyols are suitable; depending on the nature of the active substance no excipients are, however, generally required in the case of soft gelatine capsules. For the manufacture of solutions and syrups, excipients such as, for example, water, polyols, saccharose, invert sugar and glucose are suitable, for injection solutions excipients such as, for example, water, alcohols, polyols, glycerine and vegetable oils are suitable, and for suppositories, excipients such as, for examle, natural or hardened oils, waxes, fats and semi-liquid or liquid polyols are suitable.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants.

The dosage of the active substance can vary within wide limits and is, of course, fitted to the individual requirements in each particular case. In general, in the case of oral administration a dosage of about 0.1 to 20 mg/kg, preferably of about 0.5 to 4 mg/kg, per day can be appropriate for adults; however, the upper limit just given can also be exceeded if this should be found to be indicated.

EXAMPLE 1

A. Preparation of the starting material (a) A solution of 0.5 g of (S)-2-O-benzyl-1-O-octadecylglycerine and 0.16 ml of triethylamine in 2 ml of chloroform is added dropwise to a solution, cooled to 0° C., of 0.16 ml of 4-chlorobutyryl chloride in 1 ml of chloroform. The reaction mixture is stirred at room temperature, diluted with 5 ml of chloroform and washed in succession with 5 ml of 1N sodium hydroxide and 3×10 ml of water. The organic phase is dried and concentrated. The residue is chromatographed on silica gel while eluting with hexane-ether (19:1). There is obtained (R)-2-O-benzyl-1-O-(4-chlorobutyryl)-3-O-octadecylglycerine in the form of an oily residue.

(b) A solution of 0.4 g of (R)-2-O-benzyl-1-O-(4-chlorobutyryl)-3-O-octadecylglycerine in 20 ml of glacial acetic acid is treated with 0.120 g of palladium oxide and hydrogen. The catalyst is removed by filtration under suction and the filtrate is dried under reduced pressure. There is obtained (R)-1-O-(4-chlorobutyryl)-3-O-octadecylglycerine of melting point 48° C.

(c) A solution of 0.33 g of (R)-1-O-(4-chlorobutyryl)-3-O-octadecylglycerine in 10 ml of dichloroethane is treated at 80° C. with 10 ml of methyl isocyanate. The solution is evaporated and the residue is chromatographed on silica gel while eluting with ether. There is obtained (R)-1-O-(4-chlorobutyryl)-2-O-(methylcarbamoyl)-3-O-octadecylglycerine of melting point 61°-62° C. (dec.).

Preparation of the product

A solution of 0.2 g of (R)-1-O-(4-chloro-butyryl)-2-O-(methylcarbamoyl)-3-O-octadecylglycerine in 10 ml of pyridine is heated to 80° C. for 16 hours. The solution is evaporated and the residue is treated with toluene by azeotropic distillation. The residue is recrystallized from ether. There is obtained 1-[3-[[(R)-2-[(methylcarbamoyl)oxy]-3-(octadecyloxy)propoxy]carbonyl]propyl]pyridinium chloride of melting point 53°-60° C. (dec.).

EXAMPLE 2

A. Preparation of the starting material (a) A solution of 0.5 g of (S)-2-O-benzyl-1-O-octadecyl glycerine in 25 ml of dichloromethane is treated with 0.3 ml of pyridine and cooled to 0° C. The solution is treated with 0.2 ml of 2-bromoethyl chloroformate, stirred at room temperature, treated with 10 ml of water and acidified to pH 3 with 1N hydrochloric acid. The organic phase is washed with water, dried and evaporated. The residue is chromatographed on silica gel while eluting with ether/n-hexane (1:1). There is obtained (R)-2-O-benzyl-1-[(2-bromoethoxy)carbonyl]-3-O-octadecylglycerine in the form of an oil.

(b) In a manner analogous to Example 1A. (b) from (R)-2-O-benzyl-1-[(2-bromoethoxy)carbonyl]-3-O-octadecylglycerine, there is obtained (R)-1-[(2-bromoethoxy)carbonyl]-3-O-octadecylglycerine of melting point 64°-65° C. (petroleum ether).

(c) A solution of 0.26 g of (R)-1-[(2-bromo-ethoxy)carbonyl]-3-O-octadecylglycerine in 5 ml of dichloromethane is treated with a solution of 1 ml of acetic anhydride and 0.050 g of N,N-dimethylaminopyridine. The reaction mixture is treated with saturated sodium bicarbonate solution and extracted with dichloromethane. The organic phase is washed with water, dried and evaporated. By chromatography on silica gel, while eluting with n-hexane-ether (1:1), there is obtained (R)-2-O-acetyl-1-O-(2-bromoethoxy)-3-O-octadecylglycerine in the form of an oil.

B. Preparation of the product

A solution of 0.37 g of (R)-2-O-acetyl-1-O-(2-bromoethoxy)-3-O-octadecylglycerine in 10 ml of pyridine is heated to 80° C. for 3 hours. The solution is evaporated and the residue is treated with toluene by azeotropic distillation. The residue is recrystallized from acetone-ether. There is obtained 1-[2-[[[(R)-2-O-acetyl-3-(octadecyloxy)propoxy]carbonyl]oxy]ethyl]pyridinium bromide of melting point 55°-60° C. (dec.).

EXAMPLE 3

A. Preparation of the starting material (a) In a manner analogous to Example 1A. (c), (R)-1-O-octadecyl-3-O-tritylglycerine is converted into (R)-2-O-(methylcarbamoyl)-1-O-octadecyl-3-O-tritylglycerine in the form of an oil.

(b) A solution of 0.57 g of (R)-2-O-(methylcarbamoyl)-1-O-octadecyl-3-O-tritylglycerine in 15 ml of dichloromethane is treated with 0.5 ml of trifluoroacetic acid. The solution is washed with water and with sodium bicarbonate, dried and evaporated. The residue is recrystallized from dichloromethane-n-hexane. There is obtained (S)-2-O-(methylcarbamoyl)-1-O-octadecylglycerine of melting point 68°-69° C.

(c) In a manner analogous to Example 2A. (a), (S)-2-O-(methylcarbamoyl)-1-O-octadecylglycerine is converted into (R)-1-O-[(2-bromoethoxy)carbonyl]-2-O-(methylcarbamoyl)-3-O-octadecylglycerine of melting point 62°-65° C.

B. Preparation of the product

A solution of 0.15 g of (R)-1-O-[(2-bromoethoxy)carbonyl]-2-O-(methylcarbamoyl)-3-O-octadecylglycerine in 5 ml of pyridine is heated at 60° C. for 20 hours. The solution is evaporated and the residue is treated with toluene by azeotropic distillation. The residue is recrystallized from acetone. There is obtained 1-[2-[[[(R)-2-[(methylcarbamoyl)oxy]-3-(octadecyloxy)propoxy]carbonyl]oxy]ethyl]pyridinium bromide of melting point 94° C. (dec.).

EXAMPLE 4

In an manner analogous to Example 3, using thiazole in place of pyridine, there is obtained 3-[2-[[[(R)-2-[(methylcarbamoyl)oxy]-3-(octadecyloxy)propoxy]carbonyl]oxy]ethyl]thiazolium bromide of melting point 75° C. (dec.).

EXAMPLE 5

A. Preparation of the starting material

A solution of 0.17 g of (S)-2-O-methyl-1-O-octadecylglycerine in 10 ml of dichloroethane is treated with 1 ml of 2-chloroethyl isocyanate and heated at 80° C. for 25 hours. The solution is evaporated and the residue is chromatographed on silica gel. After elution with dichloromethane-ether (9:1), there is obtained (R)-1-O-[(2-chloroethyl)carbamoyl]-2-O-methyl-3-O-octadecylglycerine in the form of an oil.

B. Preparation of the product

A solution of 0.035 g of (R)-1-O-[(2-chloroethyl)carbamoyl]-2-O-methyl-3-O-octadecylglycerine is treated with 5 ml of pyridine and heated at 80° C. for 3 days. The solution is evaporated and the residue is treated with toluene by azeotropic distillation. The residue is recrystallized from acetone. There is obtained 1-[2-[1-[(R)-2-methoxy-3-(octadecyloxy)propoxy]formamido]ethyl]pyridinium chloride of melting point 65° C. (dec.).

EXAMPLE 6

A. Preparation of the starting material

In a manner analogous to Example 2A. (a), (S)-2-O-methyl-1-O-octadecylglycerine is converted into (R)-1-

O-[(2-bromoethoxy)carbonyl]-2-O-methyl-3-O-octadecylglycerine in the form of an oil.

B. Manufacture of the product

In a manner analogous to Example 2B., (R)-1-O-[(2-bromoethoxy)carbonyl]-2-O-methyl-3-O-octadecylglycerine is converted into 1-[2-[[[(R)-2-methoxy-3-(octadecyloxy)propoxy]carbonyl]oxy]ethyl]pyridinium bromide of melting point 53° C. (dec.).

EXAMPLE 7

In a manner analogous to Example 5 or 6, starting from (RS)-2-O-methyl-1-O-octadecylcarbamoyl-glycerine there is obtained
    (a)    1-[2-[1-[(RS)-2-methoxy-3-(octadecylcarbamoyloxy)propoxy]formamido]ethyl]pyridinium chloride, melting point 50°-60° C. (ethyl acetate) or
    (b)    1-[2-[[[(RS)-2-methoxy-3-[(octadecylcarbamoyl)oxy]propoxy]carbonyl]oxy]ethyl]pyridinium bromide, melting point 85°-86° C. (ethyl acetate).

EXAMPLE 8

A. Preparation of the starting material

A solution of 0.3 g of (S)-2-O-(methoxy-carbonyl)-1-O-octadecylglycerine in 15 ml of dichloroethane is treated with 2 ml of 2-chloroethyl isocyanate and heated at 80° C. for 24 hours. The solution is evaporated and the residue is recrystallized from acetone-ether. There is obtained (R)-1-O-[(2-chloroethyl)carbamoyl]-2-O(methoxycarbonyl)-3-O-octadecylglycerine of melting point 77°-78° C.

B. Preparation of the product

A solution of 0.07 g of (R)-1-O-[(2-chloroethyl)carbamoyl]-2-O-(methoxycarbonyl)-3-O-octadecylglycerine in 10 ml of pyridine is heated at 80° C. for 3 days. The solution is evaporated and the residue is recrystallized from acetone-n-hexane. There is obtained 1-[1-[(R)-2-[(methoxycarbonyl]oxy]-3-(octadecyloxy)-propoxy]formamido]-ethyl]pyridinium chloride of melting point 83° C. (dec.).

EXAMPLE 9

In a manner analogous to Example 8B., using thiazole in place of pyridine there is obtained 3-[2-[1[(R)-2-[methoxycarbonyl)oxy]-3-(octadecyloxy)propoxy]formamido]ethyl]thiazolium chloride of melting point 72° C.

EXAMPLE 10

A. Preparation of the starting material

In a manner analogous to Example 2A. (a), from (S)-2-O-(methoxycarbonyl)-1-O-octadecylglycerine there is obtained (R)-1-O-[(2-bromoethoxy)carbonyl]-2-O-(methoxycarbonyl)-3-O-octadecylglycerine in the form of an oil.

B. Preparation of the product

In a manner analogous to Example 6B., from (R)-1-O-[(2-bromoethoxy)carbonyl]-2-O-(methoxycarbonyl)-3-O-octadecylglycerine, there is obtained 1-[2-[[(R)-2-[(methoxycarbonyl)oxy]-3-(octadecyloxy)propoxy]carbonyl]oxy]ethyl]pyridinium bromide of melting point 84°-85° C. (dec.).

EXAMPLE 11

In a manner analogous to Example 10B., from (R)-1-O-[(2-bromoethoxy)carbonyl]-2-O-(methoxycarbonyl)-3-O-(octadecylcarbamoyl)glycerin, there is obtained 1-[2-[[[(R)-2-[(methoxycarbonyl)oxy]-3-(octadecylcarbamoyl)oxy]propoxy]carbonyl]oxy]ethyl]pyridinium bromide of melting point 54° C. (dec.). The starting material can be obtained in analogy to Example 10A.

EXAMPLE 12

In a manner analogous to Example 10B., using thiazole in place of pyridine there is obtained 3-[2-[[[(R)-2-[(methoxycarbonyl)oxy]-3-(octadecyloxy)propoxy]carbonyl]oxy]ethyl]thiazolium bromide of melting point 147° C. (dec.).

EXAMPLE 13

A. Preparation of the starting material (a) In a manner analogous to Example 5A., from (S)-2-O-benzyl-1-O-octadecylglycerine, there is obtained (R)-2-O-benzyl-1-O-[(2-chloroethyl)carbamoyl]-3-O-octadecylglycerine in the form of an oil.

(b) In a manner analogous to Example 1A. (b), from (R)-2-O-benzyl-1-O-[(2-chloroethyl)carbamoyl]-3-O-octadecylglycerine, there is obtained (R)-1-[(2-chloroethyl)carbamoyl]-3-O-octadecylglycerine of melting point 70° C.

(c) In a manner analgous to Example 1A. (c), from (R)-1-[(2-chloroethyl)carbamoyl]-3-O-octadecylglycerine, there is obtained (R)-1-O-[(2-chloroethyl)carbamoyl]-2-O-(methylcarbamoyl)-3-O-octadecylglycerine of melting point 91°-92° C.

B. Preparation of the product

In a manner analogous to Example 8B., from (R)-1-O-[(2-chloroethyl)carbamoyl]-2-O-(methylcarbamoyl)-3-O-octadecylglycerine, there is obtained 1-[2-[1-[(R)-(2-methylcarbamoyl)-3-(octadecyloxy)propoxy]formamido]ethyl]pyridinium chloride, MS:M+ =550.

EXAMPLE 14

A. Preparation of the starting material (a) 2 g of sodium azide were added to a solution of 7.75 g of (RS)-1-O-octadecyl-2-O-tosyl-3-O-tritylglycerine in 75 ml of dry dimethylformamide. The suspension was stirred at 100° C. for 3 hours with the exclusion of moisture. After removing the solid material, by filtration the solvent was removed by distillation and the residue was chromatographed on silica gel with toluene-pyridine (99:1 in vol.). After crystallization from n-hexane, there were obtained 4.05 g of (RS)-1-O-octadecyl-2-deoxy-2-azido3-O-tritylglycerine (63.3% of theory), melting point 58°-59° C.

(b) A solution of 3.6 g of (RS)-1-O-octadecyl-2-deoxy-2-azido-3-O-tritylglycerine in 20 ml of dry ether was added drowise with the exclusion of moisture to a suspension of 130 mg of lithiumaluminumhydride in 50 ml of dry ether. After the evolution of nitrogen had ended, the mixture was stirred at room temperature for 10 minutes. Ice cubes were then added and the reaction mixture was stirred for 30 minutes. The ether phase was then separated. The solid phase was washed with ether and the combined ether phases were dried. After removing the solvent, by distillation, the residue was chromatographed on a silica gel column with ether-methanol (9:1 in vol.). After crystallization from n-hexane, there were obtained 3.1 g of (RS)-1-O-octadecyl-2-deoxy-2-amino-3-O-tritylglycerine (90.1% of theory), melting point 56°-57° C.

(c) 5 ml of 25% aqueous hydrochloric acid were added to a solution, heated to 95° C., of 4.65 g of (RS)-1-O-octadecyl-2-deoxy-2-amino-3-O-tritylglycerine in 100 ml of dioxane and the reaction mixture was held at 95° C. for 30 minutes. Upon cooling, there were obtained 2.75 g (yield: 87.4%) of (RS)-1-O-octadecyl-2-deoxy-2-aminoglycerine hydrochloride, melting point 110°–111° C.

(d) 1.4 go of potassium hydroxide in 5 ml of water were added dropwise while stirring to a solution of 2.75 g of (RS)-1-O-octadecyl-2-deoxy-2-aminoglycerine hydrochloride in 30 ml of methanol. The methanol was then removed by distillation. Ten (10) ml of water and 100 ml of dichloromethane were added to the residue. 0.89 g of methyl chloroformate were added dropwise to the mixture while stirring. After stirring at room temperature for 1½ hours, the phases were separated in a separating funnel. The organic phase was washed with water, dried and, after distilling the solvent and the excess reagent, the residue was crystallized from n-hexane. There were obtained 2.90 g of (RS)-1-O-octadecyl-2-deoxy-2-(1-methoxyformamido)glycerine (100% yield), melting point 63°–64° C.

(e) 0.2 ml of 2-chloroethyl chloroformate (1.4 mmol) in 2 ml of chloroform was added dropwise with the exclusion of moisture to a solution of 0.4 of (RS)-1-O-octadecyl-2-deoxy-2-(1-methoxyformamido)glycerine (1 mmol) in 5 ml of chloroform and 0.25 ml of pyridine in an ice-bath. The reaction mixture was stirred at room temperature for 2 hours. After working-up the reaction mixture was filtered over silica gel with ether and the product was crystallized from n-hexane. There was obtained 0.475 g of (RS)-1-O-[(2-chloroethoxy)carbonyl]-2-deoxy-2-(1-methoxyformamido)-3-O-octadecylglycerine (93.5% of theory), melting point 58°–59° C.

B. Preparation of the product, 1-[2-[[[(RS)-2-(1-methoxyformamido)-3-octadecyloxy]propoxy]oxy]ethyl]pyridinium chloride 0.3 g of (RS)-1-O-[(2-chloroethoxy)carbonyl]-2-deoxy-2-(1-methoxyformamide)-3-O-octadecylglycerine was reacted with 5 ml of dry pyridine at 80° C. for 24 hours. The product was chromatographed on silica gel with chloroform-methanol (7:3) and then with chloroform-methanol-water (60:35:5). The product, dissolved in methanol, was then subjected to a percolation through 10 ml of an anion exchanger in the Cl⁻ form. There were obtained 125 mg of a beige compound (36% of theory), melting point 152°–154° C.

EXAMPLE 15

A. Preparation of the starting material

In a manner analogous to Example 14A.e), (RS)-1-O-octadecyl-2-deoxy-2-(1-methoxyformamido)glycerine was converted with 3-chloropropionyl chloride into (RS)-1-O-(3-chloropropionyl)-2-deoxy-2-(1-methoxyformamido)-3-O-octadecylglycerine of melting point 65°–66° C.

B. Preparation of the product

In a manner analgous to Example 14B., (RS)-1-O-(3-chloropropionyl)-2-deoxy-2-(1-methoxyformamido)-3-O-octadecylglycerine were converted into 1-[2-[[[(RS)-2-(1-methoxyformamido)-3-(octadecyloxy)propoxy]carbonyl]oxy]ethylpyridinium chloride, melting point 190°–192° C.

EXAMPLE 16

In a manner analogous to Example 15, (RS)-1-O-octadecyl-2-deoxy-2-(1-methoxyformamido)glycerine was converted with 4-chlorobutyryl chloride into (RS)-1-O-octadecyl-2-deoxy-2-(1-methoxyformamido)-3-O-(4-chlorobutyryl)glycerine, melting pont 73°–74° C., and the latter was converted into 1-[3-[[[(RS)-2-(1-methoxyformamido)-3-(octadecyloxy)propoxy]carbonyl]oxy]propyl]pyridinium chloride, melting point 200° C. (dec.)

EXAMPLE 17

A. Preparation of the starting material 0.75 g of (RS)-1-O-octadecyl-2-deoxy-2-(1-methoxyformamido)glycerine was reacted with 1 ml of 2-chloroethyl isocyanate at 100° C. for 2 hours with the exclusion of moisture. After completion of the reaction the excess reagent was removed by distillation and the residue was crystallized from n-hexane. There are obtained 0.88 g (92.8% of theory) of (RS)-1-O-[(2-chloroethyl)carbamoyl]-2-deoxy-2-(1-methoxyformamido)-3-O-octadecylglycerine, melting point 73°–74° C.

B. Preparation of the product

In a manner analogous to Example 14B., (RS)-1-O-[(2-chloroethyl)carbamoyl]-2-deoxy-2-(1-methoxyformamido)-3-O-octadecylglycerine was converted into 1-[2-[1-[(RS)-2-(1-methoxyformamido)-3-(octadecyloxy)propoxy]formamido]ethyl]pyridinium chloride, melting point 195°–197° C.

EXAMPLE 18

A. Preparation of the starting material (a) In a manner analogous to Example 14A. (a), (RS)-1-O-octadecyl-3-O-tosylglycerine was converted into (RS)-1-O-octadecyl-3-deoxy-3-azidoglycerine, melting point 42° C. (n-hexane).

(b) A solution of 5 g of (RS)-1-O-octadecyl-3-deoxy-3-azidoglycerine in 75 ml of tetrahydrofuran was hydrogenated with 2.5 g of 10% palladium-carbon under normal pressure and at room temperature. After 3 hours the catalyst was removed by filtration, the solvent was removed by distillation and the product, (RS)-1-O-octadecyl-3-deoxy-3-deoxy-3-aminoglycerine, was crystallized from chloroform-hexane. There were obtained 4.1 g of white crystals (88.2% of theory); melting point 68° C.

(c) 2 ml of an aqueous solution of 0.5 g of potassium hydroxide were added to a solution of 1.72 g of (RS)-1-O-octadecyl-3-deoxy-3-aminoglycerine in 20 ml of dichloromethane. While stirring, the two-phase system 0.7 ml of 2-bromoethyl chloroformate (corresponding to 1.035 g or 5.52 mmol) was added dropwise. After stirring at room temperature for 1 hour, the phases were separated. The organic phase was washed with water and dried. The solvent and the excess reagent were removed by distillation, and the residue was crystallized from n-hexane. There were obtained 2.1 g (84.8% of theory) of (RS)-1-O-octadecyl-3-deoxy-3-[1-(2-bromo)-ethoxyformamido]glycerine, melting point 72°–74° C.

(d) 0.5 g of (RS)-1-O-octadecyl-3-deoxy-3-[1-(2-bromo) ethoxyformamido]glycerine was reacted with 2 ml of methyl isocyanate in the presence of 0.05 ml of diisopropylethylamine at 40° C. (reflux) for 2 hours. The excess reagent was subsequently removed by distillation and the residue was crystallized from n-hexane.

There was obtained 0.49 g (87.9% of theory) of (RS)-1-O-octadecyl-2-O(methylcarbamoyl)-3-deoxy-3-[1-(2-bromo)ethoxyformamido]glycerine, melting point 91°-92° C.

B. Preparation of the product 2 ml of dry pyridine were added to a solution of 0.3 g of (RS)-1-O-octadecyl-2-O-(methylcarbamoyl)-3-deoxy-3-[1-(2-bromo)ethoxyformamido]glycerine in 1 ml of nitromethane. The mixture was left to react at 80° C. for 24 hours. The working-up and purification were carried out in analogy to Example 14B., with the exception that the ion exchanger was present in the Br⁻ form. There was obtained 0.1 g (26.1% of theory) of 1-[2-[[(RS)-2-[(methylcarbamoyl)oxy]-3-(octadecyloxy)-propyl]carbamoyl]ethyl]pyridinium bromide, melting point 195° C. (dec.).

EXAMPLE 19

(a) Analogously to Example 1, there was prepared 3-methyl-1-[3-[[(R)-[(methylcarbamoyl)oxy]-3-(octadecyloxy)propoxy]carbonyl]propylimidazolium chloride in the form of a wax, MS:M+ =552;

(b) analogously to Example 3 there was prepared 1-[2-[[[(S)-[(methylcarbonyl)oxy]-3-(octadecyloxy)-propoxy]carbonyl]oxy]ethyl]pyridinium bromide, m.p. 96° C. (dec.);

(c) analogously to Example 6 there was prepared 1-[2-[[[3-methoxy-2(R)-octadecyloxy)propoxy]carbonyl]-oxy]ethyl]pyridinium bromide, m.p. 47° C. from acetone (dec.);

(d) analogously to Example 5 and 16 there was prepared 1-[3-[[(R)-2-(benzyloxy)-3-(octadecyloxy)propoxy]-carbonyl]propyl]pyridinium chloride in the form of a wax; MS:M+ =582;

(e) analogously to Example 8 there was prepared 1-[2-[1-[(R)-2-[(methoxycarbonyl)oxy]-1-[(octadecyloxy)methyl]ethoxy]formamido]ethyl]pyridinium chloride, m.p. 57° C.

EXAMPLE 20

Analogously to Example 7b and Example 15 there were prepared
(a) 1-[3-[[(RS)-2-methoxy-3-O-[(octadecylcarbamoyl)oxy]propoxy]carbonyl]propyl]pyridinium chloride in the form of a colorless wax, MS:M+ =549;
(b) 3-[3-[[(RS)-2-methoxy-3-[(octadecylcarbamoyl)oxy]propoxy]carbonyl]propyl]thiazolium chloride, m.p. 60°-62° C. from ethyl acetate.

EXAMPLE 21

Analogously to Example 11 and Example 16 there were prepared
(a) 1-[3-[[(RS)-2-[(methoxycarbonyl)oxy]-3-[(octadecylcarbamoyl)oxy]propoxy]carbonyl]propyl]-pyridinium chloride, m.p. 51° C.;
(b) 1-[3-[[(R)-2-[(methoxycarbonyl)oxy]-3-[(octadecylcarbamoyl)oxy]propoxy]carbonyl]propyl]pyridinium chloride, m.p. 55° C.;
(c) 1-[3-[[(S)-2-[(methoxycarbonyl)oxy]-3-[[(octadecylcarbamoyl)oxy]propoxy]carbonyl]propyl]pyridinium chloride, MS:M+ =593;
(d) 1-[3-[[(S)-2-[(methoxycarbonyl)oxy]-3-(octadecylcarbamoyl)oxy]propoxy]carbonyl]propyl]pyridinium iodide, MS:M+ =593;
(e) 3-[3-[[(R)-2-[(methoxycarbonyl)oxy]-3-[(octadecylcarbamoyl)oxy]propoxy]carbonyl]propyl]thiazolium iodide m.p. 64° C. (dec.);
(f) 3-[3-[[(S)-2-[(methoxycarbonyl)oxy]-3-[(octadecylcarbamoyl)oxy]propoxy]carbonyl]propyl]thiazolium iodide, m.p. 71° C.

EXAMPLE 22

Analogously to the above Examples there were prepared
(a) 1-[4-[2-[(methylcarbamoyl)oxy]-3-(octadecyloxy)propoxy]butyl]pyridinium bromide, m.p. 193° C.;
(b) 1-[3-[[(RS)-2-[(methylcarbonyl)oxy]-3-(octadecanoyloxy)propoxy]carbonyl]propyl]pyridinium chloride in the form of a wax, MS:M+ =564.

EXAMPLE 23

A. Preparation of the starting material (a) 15.35 g of (RS)-1-O-benzyl-3-O-tritylglycerine (Helv. Chim. Acta 65, 1982, 1059) were dissolved in 75 ml of chloroform. 10 ml of pyridine were added, followed by 10.5 g of tosyl chloride. After 24 hours at room temperature the chloroform was removed by distillation. The residue was taken up in 50 ml of pyridine, 10 ml of water and then 10 g of potassium bicarbonate were added. After removing the solvent by distillation, the residue was taken up in toluene, the solid material was separated, the organic phase was then shaken out with water, dried and evaporated. The product crystallized from a melt upon cooling. Yield 95%, m.p. 98°-100° C.

(b) Analogously to Example 14A (a) to 14A (d) the (RS)-1O-benzyl-2-O-tosyl-3-O-tritylglycerine obtained was converted in succession into
(RS)-1-O-benzyl-2-deoxy-2-azido-3-O-tritylglycerine,
(RS)-1-O-benzyl-2-deoxy-2-amino-3-O-tritylglycerine, m.p. 67°-69° C.,
(RS)-1-O-benzyl-2-deoxy-2-aminoglycerine hydrochloride m.p. 148°-149° C., and
(RS)-1-O-benzyl-2-deoxy-2-(1-methoxyformamido)-glycerine.

(c) 0.45 g of (RS)-1-O-benzyl-2-deoxy-2-(1-methoxyformamido)glycerine was treated with 0.6 g of octadecyl isocyanate and the solution was heated to 90° C. for 1 hour. The mixture was chromatographed on silica gel with a mixture of toluene and ethyl acetate (4:1). After crystallization from n-hexane, there was obtained 0.65 g of (RS)-1-O-benzyl-2-deoxy-2-(1-methoxyformamido)-3-O-(octadecylcarbamoyl)glycerine, m.p. 65°-67° C.

(d) 4.9 g of (RS)-1-O-benzyl-2-deoxy-2-(1-methoxyformamido)-3-O-(octadecylcarbamoyl)glycerine dissolved in 75 ml of tetrahydrofuran were hydrogenated in the presence of 1 g of 10% palladium-carbon under a slight hydrogen excess pressure. 4.05 g of (RS)-2-deoxy-2-(1-methoxyformamido)-1-O-octadecylcarbamoyl-glycerine were obtained, m.p. 86° C. (from n-hexane).

(e) 0.75 ml of 4-chlorobutyryl chloride in 5 ml of chloroform was added dropwise with the exclusion of moisture to a solution of 2 g of (RS)-2-deoxy-2-(1-methoxyformamido)-1-O-octadecylcarbamoylglycerine (4.5 mmol) in 20 ml of chloroform and 0.7 ml of triethylamine in an ice-bath. The reaction mixture was stirred at room temperature for 2 hours. After working-up, the reaction product was filtered on silica gel with dichloromethane/ether (1:1). 2.3 g of (RS)-1-O-(4-chlorobutyryl)-2-deoxy-2-(1-methoxyformamido)-3-O-(octadecylcarbamoyl)glycerine were obtained after crystallization from n-hexane, m.p. 68°-70° C.

B. Preparation of the product

Analogously to Example 14B, from 0.4 g of the chloride obtained under A(e) there was obtained 0.2 g of 1-[3-[[(RS)-2-(1-methoxyformamido)-3-(octadecylcarbamoyloxy)propoxy]carbonyl]propyl]pyridinium chloride (44% of theory), m.p. 200° C. (dec.).

EXAMPLE 24

Analogously to Example 23B., there was obtained 1-[3-[[(RS)-2-(1-methoxyformamido)-3-(octadecylcarbamoyloxy)propoxy]carbonyl]propyl]thiazolium chloride, m.p. 180° C. (dec.).

EXAMPLE 25

A. Preparation of the starting material (a) Analogously to Example 14A (a) and (b), (RS)-1-O-tosyl-3-O-benzylglycerine (Helv. Chim. Acta 65, 1982, 1059) was converted via (RS)-1-deoxy-1-azido-3-O-benzylglycerine into
(RS)-1-deoxy-1-amino-3-O-benzylglycerine, m.p. 76°–77° C.

(b) 0.33 g of (RS)-1-deoxy-1-amino-3-O-benzylglycerine was dissolved in 20 ml of dichloromethane and treated with 0.8 g of stearoyl chloride. The mixture was stirred in the presence of an aqueous solution of potassium hydroxide. The (RS)-1-deoxy-1-octadecanamido-3-O-benzylglycerine obtained from the organic phase was chromatographed on silica gel with ether. After crystallization from n-hexane, there was obtained 0.5 g of crystals, m.p. 72°–73° C.

(c) 0.45 g of (RS)-1-deoxy-1-octacecanamido-3-O-benzylglycerine was acetylated with 0.2 g of acetic anhydride and 20 mg of 4-dimethylaminopyridine as the catalyst. After working-up, filtration on silica gel with hexane/ether (1:1) and crystallization in n-hexane, there was obtained 0.49 g of (RS)-1-deoxy-1-octadecanamido-2-O-acetyl-3-O-benzylglycerine, m.p. 53°–55° C.

(d) Analogously to Example 23A (d) and (e), this benzyl ether was converted via
(RS)-1-deoxy-1-octadecanamido-2-O-acetylglycerine m.p. 66°–68° C. (from n-hexane), into
(RS)-2-O-acetyl-1-O-(4-chlorobutyryl)-3-deoxy-3-octadecanamidoglycerine, m.p. 55°–56° C.

B. Preparation of the product

Analogously to Example 14B, from 0.3 g of (RS)-2-O-acetyl-1-O-(4-chlorobutyryl)-3-deoxy-3-octadecanamidoglycerine, there was obtained 0.16 g of 1-[3-[[(RS)-2-acetoxy-3-octadecanamidopropoxy]carbonyl]propyl]pyridinium chloride (46% of theory), m.p. 220° C. (dec.).

EXAMPLE 26

A. Preparation of the starting material (a) A solution of 0.9 g of (RS)-1-deoxy-1-amino-3-O-benzylglycerine in 20 ml of dichloromethane was added to an aqueous potassium hydroxide solution. A solution of 1.7 g of octadecyl chloroformate in 10 ml of dichloromethane was added dropwise to the mixture while stirring. After stirring at room temperature for 1 hour, the mixture was worked-up and the compound obtained was chromatographed on silica gel with n-hexane/ether (1:1). After crystallization from n-hexane, there were obtained 1.6 g of crystals, m.p. 58°–59° C.

(b) 2.2 g of (RS)-1-deoxy-1-[1-(octadecyloxy)formamido]-3-O-benzylglycerine were acylated with methyl chloroformate to give 2.15 g of (RS)-1-deoxy-1-[1-(octadecyloxy)formamido]-2-O-methoxycarbonyl-3-O-benzylglycerine, m.p. 52°–54° C. (from n-hexane).

(c) Analogously to Example 23A (d) and (e), from the resulting benzyl ether there was obtained via
(RS)-1-deoxy-1-[1-(octadecyloxy)formamido]-2-O-methoxycarbonylglycerine, m.p. 56°–57° C. (from n-hexane),
(RS)-1-deoxy-1-[1-(octadecyloxy)formamido]-2-O-methoxycarbonyl-3-O-(4-chlorobutyryl)glycerine.

B. Preparation of the product

Analogously to Example 14B, 0.4 g of (RS)-1-deoxy-1-[1-(octadecyloxy)formamido]-2-O-methoxycarbonyl-3-O-(4-chlorobutyryl)glycerine was converted into 0.15 g of 1-[3-[[(RS)-2-[(methoxycarbonyl)oxy[-3-[1-(octadecyloxy)-formamido]propoxy]carbonyl]propyl]pyridinium chloride, (31.8% of theory), m.p. 168° C.

EXAMPLE A

A compound of formula I can be used as follows as the active substance for the preparation of pharmaceutical preparations:

| (a) Tablets | 1 tablet contains |
|---|---|
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and granulated with a 10 percent solution of hydroxypropylmethylcellulose in a mixture of isopropanol and methylene chloride. The granulate is dried, sieved and mixed with the remainder of the adjuvants. It is then pressed on a press to biplanar tablets of 12 mm diameter with a break-bar.

| (b) Capsules | 1 capsule contains |
|---|---|
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and sieved. After renewed mixing, the capsule fill mass obtained is filled into interlocking gelatine capsules of suitable size on a fully automatic capsule filling machine.

We claim:

1. A compound of the formula

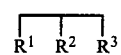

I wherein one of the residues $R^1$, $R^2$ and $R^3$ is group U of the formula $-X^1-C(O)-(A^1)_n-Z^1$, another of the residues is group V of the formula $-X^2-C(O)-A^2-Z^2$ and the remaining residue is group W of the formula $-X^3T-(C_{2-6}\text{-alkylene})-N^+(\text{Het})Q^-$ whereby one of $-X^1$, $-X^2$ and $-X^3$ is oxygen or NH

17 and the other two are oxygen, $A^1$ and $A^2$, independently, are oxygen or NH, n is the integer 1 or 0, $Z^1$ is $C_{9-25}$-alkyl or $C_{9-25}$-alkenyl, $Z^2$ is $C_{1-5}$-alkyl, $C_{2-5}$-alkenyl, or phenyl-T is carbonyl, C(O)O or C(O)NH or, when $X^3$ is oxygen, T is also methylene, $-N^+(Het)$ is selected from the group consisting of oxazolium, isoxazolium, pyridazinium, quinolinium, isoquinolinium, N-methylimidazolium, pyridinium and thiazolium, and $-Q^-$ is the anion of a strong inorganic or organic acid, or its hydrate.

2. A compound in accordance with claim 1, wherein $R^3$ is group W.

3. A compound, in accordance with claim 2, wherein $R^1$ is octadecylcarbamoyloxy.

4. A compound, in accordance with claim 3, wherein $R^2$ is methoxy or methoxycarbonyloxy.

5. A compound, in accordance with claim 4, wherein $R^3$ is 4-(1-pyridinium chloride)-n-butyryloxy, 4-(1-pyridinium iodide)-n-butyryloxy, 4-(3-thiazolium chloride)-n-butyryloxy or 4-(3-thiazolium iodide)-n-butyryloxy.

6. A compound, in accordance with claim 5, wherein $R^1$ is octadecylcarbamoyloxy; $R^2$ is methoxycarbonyloxy; and $R^3$ is 4-(1-pyridinium chloride)-n-butyryloxy, 4-(1-pyridinium iodide)-n-butyryloxy, 4-(3-thiazolium chloride)-n-butyryloxy or 4-(3-thiazolium iodide)-n-butyryloxy.

7. A compound, in accordance claim 6, wherein $R^1$ is octadecylcarbamoyloxy, $R^2$ is methoxycarbonyloxy and $R^3$ is 4-(thiazolium iodide)-n-butyryloxy, that is, 3-[3-[[(R)-2-(Methoxycarbonyloxy)-3-[(octadecylcarbamoyl)oxy]propoxy]carbonyl]propyl]thiazolium iodide.

8. A compound selected from the group consisting of 3-[3-[[(S)-2-[(methoxycarbonyl)oxy]-3-[(octadecylcarbamoyl)oxy]propoxy]carbonyl]propyl]thiazolium iodide,
1-[3-[[(RS)-2-[(methoxycarbonyl)oxy[-3-(octadecylcarbamoyl)oxy]propoxy]carbonyl]propyl]-pyridinium chloride,
1-[3[[(RS)-2-(1-methoxyformamido)-3-(octadecylcarbamoyloxy)propoxy]carbonyl]propyl]thiazolium chloride,
1-[3-[[(S)-2-[(methoxycarbonyl)oxy]-3-[(octadecylcarbamoyl)oxy propoxy]carbonyl]propyl]-pyridinium iodide, and
1-[3-[[(R)-2-[(methoxycarbonyl)oxy]-3-[(octadecylcarbamoyl)oxy propoxy]carbonyl]propyl]-pyridinium chloride.

9. A compound of the formula

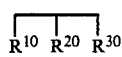

VII wherein one of the residues $R^{10}$, $R^{20}$ and $R^{30}$ is group U of the formula $-X^1-C(O)-(A^1)_n-Z^1$, another of the residues is group V of the formula $-X^2-C(O)-(A^2)_p-Z^2$, and the remaining residue is group W of the formula $-X^3T-(C_{2-6}\text{-alkylene})-N^+(Het)Q^-$, wherein one of $-X^1$, $-X^2$ and $-X^3$ is oxygen or NH and the other two are oxygen, $A^1$ and $A^2$, independently, are oxygen or NH, n and p are the integer 1 or 0, $Z^1$ is $C_{9-25}$-alkyl or $C_{9-25}$-alkenyl, $Z^2$ is $C_{1-5}$-alkyl, $C_{2-5}$-alkenyl, or phenyl, T is carbonyl, C(O)O or C(O)NH or, when $X^3$ is oxygen, T is also methylene, $-N^+(Het)$ is selected form the group consisting of oxazolium, isoxazolium, pyridazinium, quinolinium, isoquolinium, N-methylimidazolium, pyridinium and

18 thiazolium and $Q^-$ is the anion of a strong inorganic or organic acid; provided that an amino group or an azido group is present in place of one of the groups U and V.

10. A pharmaceutical composition for inhibiting blood platelet activating factor comprising an effective amount of a compound of the formula

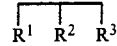

wherein one of the residues $R^1$, $R^2$ and $R^3$ is group U of the formula $-OY^1$ or $-X^1-C(O)-(A^1)_n-Z^1$, another of the residues is group V of the formula $-OY^2$ or $-X^2-C(O)-(A^2)_p-Z^2$, and the remaining residue is group W of the formula, $-X^3T-(C_{2-6}\text{-alkylene})-N^+(Het)Q^-$
wherein one of $X^1$, $-X^2$ and $X^3$ is oxygen or NH and the other two are oxygen,
$Y^1$ is $C_{10-26}$-alkyl or $C_{10-26}$-alkenyl,
$Y^2$ is $C_{1-6}$-alkyl, $C_{2-6}$-alkenyl,
$C_{3-6}$-cycloalkyl, $C_{5-6}$-cycloalkenyl, phenyl, benzyl or 2-tetrahydropyranyl,
$A^1$ and $A^2$, independently, are oxygen or NH,
n and p are the integer 1 or 0,
$Z^1$ is $C_{9-25}$-alkyl or $C_{9-25}$-alkenyl,
$Z^2$ is $C_{1-5}$-alkyl, $C_{2-5}$-alkenyl, phenyl or, when $(A^2)_p$ is not oxygen, $Z^2$ is also hydrogen,
T is carbonyl, C(O)O or C(O)NH or, when $X^3$ is oxygen, T is also methylene,
$-N^+(Het)$ is selected from the group consisting of oxazolium, isoxazolium, pyridazinium, quinolinium, isoquinolinium, N-methylimidazolium, pyridinium and thiazolium, and
$Q^-$ is the anion of a strong inorganic or organic acid, provided that when $R^1$ is a group of the formula $-OY^1$ or $-OY^2$, $R^2$ is a group V or $OY^1$, and $X^3$ is oxygen, then T is C(O)O or C(O)NH, or its hydrate.

11. A pharmaceutical composition in accordance with claim 10, wherein $R^3$ is group W.

12. A pharmaceutical composition, in accordance with claim 11, wherein $R^1$ is octadecylcarbamoyloxy.

13. A pharmaceutical composition, in accordance with claim 12, wherein $R^2$ is methoxy or methoxycarbonyloxy.

14. A pharmaceutical composition, in accordance with claim 13, wherein $R^3$ is 4-(1-pyridinium chloride)-n-butyryloxy, 4-(1-pyridinium iodide)-n-butyryloxy, 4-(3-thiazolium chloride)-n-butyryloxy or 4-(3-thiazolium iodide)-n-butyryloxy.

15. A pharmaceutical composition, in accordance with claim 14, wherein $R^1$ is octadecylcarbamoyloxy; $R^2$ is methoxycarbonyloxy; and $R^3$ is 4-(1-pyridinium chloride)-n-butyryloxy, 4-(1-pyridinium iodide)-n-butyryloxy, 4-(3-thiazolium chloride)-n-butyryloxy or 4-(3-thiazolium iodide)-n-butyryloxy.

16. A pharmaceutical composition, in accordance with claim 15, wherein $R^1$ is octadecylcarbamoyloxy, $R^2$ is methoxycarbonyloxy and $R^3$ is 4-(3-thiazolium iodide)-n-butyryloxy, that is, 3-[3-[[(R)-2-(Methoxycarbonyloxy)-3-[(octadecylcarbamoyl)oxy]propoxy]carbonyl]propyl]thiazolium iodide.

17. A method of inhibiting blood platelet activating factor which comprises administering to a host requiring such treatment an effective amount of a compound of the formula

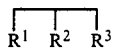

wherein one of the residues $R^1$, $R^2$ and $R^3$ is group U of the formula $-OY^1$ or $-X^1-C(O)-(A^1)_n-Z^1$, another of the residues is group V of the formula $-OY^2$ or $-X^2-C(O)-(A^2)_p-Z^2$, and the remaining residue is group W of the formula, $-X^3T-(C_{2-6}\text{-alkylene})-N^+(Het)Q^-$ wherein one of $X^1$, $-X^2$ and $X^3$ is oxygen or NH and the other two are oxygen, $Y^1$ is $C_{10-26}$-alkyl or $C_{10-26}$-alkenyl, $Y^2$ is $C_{1-6}$-alkyl, $C_{2-6}$-alkenyl, $C_{3-6}$-cycloalkyl, $C_{5-6}$-cycloalkenyl, phenyl, benzyl or 2-tetrahydropyranyl, $A^1$ and $A^2$, independently, are oxygen or NH, n and p are the integer 1 or 0, $Z^1$ is $C_{9-25}$-alkyl or $C_{9-25}$-alkenyl, $Z^2$ is $C_{1-5}$-alkyl, $C_{2-5}$-alkenyl, phenyl or, when $(A^2)_p$ is not oxygen, $Z^2$ is also hydrogen, T is carbonyl, C(O)O or C(O)NH or, when $X^3$ is oxygen, T is also methylene, $-N^+(Het)$ is selected from the group consisting of oxazolium, isoxazolium, pyridazinium, quinolinium, isoquinolinium, N-methylimidazolium, pyridinium and thiazolium, and $Q^-$ is the anion of a strong inorganic or organic acid, provided that when $R^1$ is a group of the formula $-OY^1$ or $-OY^2$, $R^2$ is a group V or $OY^1$, and $X^3$ is oxygen, then T is C(O)O or C(O)NH, or its hydrate.

18. A method in accordance with claim 17, wherein $R^3$ is group W.

19. A method, in accordance with claim 18, wherein $R^1$ is octadecylcarbamoyloxy.

20. A method in accordance with claim 19, wherein $R^2$ is methoxy or methoxycarbonyloxy.

21. A method, in accordance with claim 20, wherein $R^3$ is 4-(1-pyridinium chloride)-n-butyryloxy, 4-(1-pyridinium iodide)-n-butyryloxy, 4-(3-thiazolium chloride)-n-butyryloxy or 4-(3-thiazolium iodide)-n-butyryloxy.

22. A method, in accordance with claim 21, wherein $R^1$ is octadecylcarbamoyloxy; $R^2$ is methoxycarbonyloxy; and $R^3$ is 4-(1-pyridinium chloride)-n-butyryloxy, 4-(1-pyridinium iodide)-n-butyryloxy, 4(3-thiazolium chloride)-n-butyryloxy or 4-(thiazolium iodide)-n-butyryloxy.

23. A method, in accordance with claim 22, wherein the compound is 3-[3-[[(R)-2-(methoxycarbonyloxy)-3[(octadecylcarbamoyl)oxy]propoxy]carbonyl]propyl]-thiazolium iodide.

* * * * *